US008600514B1

(12) United States Patent
Carroll (10) Patent No.: US 8,600,514 B1
(45) Date of Patent: *Dec. 3, 2013

(54) METHODS FOR IMPROVING MOBILITY AND CONTROLLING CARTILAGE MATRIX DEGRADATION OF WEIGHT-BEARING ARTICULAR JOINTS

(75) Inventor: William J. Carroll, La Center, WA (US)

(73) Assignee: International Rehahilitative Sciences, Inc., Vancouver, WA (US)

( * ) Notice: Subject to any disclaimer, the term of this patent is extended or adjusted under 35 U.S.C. 154(b) by 473 days.

This patent is subject to a terminal disclaimer.

(21) Appl. No.: 12/950,601

(22) Filed: Nov. 19, 2010

Related U.S. Application Data

(63) Continuation of application No. 12/016,914, filed on Jan. 18, 2008, now Pat. No. 8,060,210, which is a continuation-in-part of application No. 10/659,278, filed on Sep. 11, 2003, now abandoned.

(60) Provisional application No. 60/409,589, filed on Sep. 11, 2002.

(51) Int. Cl.
*A61N 1/04* (2006.01)
(52) U.S. Cl.
USPC .......................................................... 607/48
(58) Field of Classification Search
USPC .......................................................... 607/48
See application file for complete search history.

(56) References Cited

U.S. PATENT DOCUMENTS

| | | |
|---|---|---|
| 3,083,712 A | 4/1963 | Keegan |
| 3,881,494 A | 5/1975 | Paul, Jr. |
| 3,902,502 A | 9/1975 | Liss et al. |
| 4,165,750 A | 8/1979 | Aleev et al. |
| 4,421,336 A * | 12/1983 | Petrofsky et al. ............. 280/252 |
| 4,669,477 A | 6/1987 | Ober |
| 4,724,842 A | 2/1988 | Charters |

(Continued)

FOREIGN PATENT DOCUMENTS

| | | |
|---|---|---|
| JP | 2000126312 A | 5/2000 |
| JP | 2001005601 A | 1/2001 |

(Continued)

OTHER PUBLICATIONS

Fowler et al., "An Evaluation of the Analgesic Effects of Meloxicam in Addition to Epidural Morphine/Mepivacaine in Dogs Ungergoing Cranial Cruciate Ligament Repair," Can. Vet. J., vol. 44, Aug. 2003, pp. 643-648.

(Continued)

*Primary Examiner* — George Manuel
(74) *Attorney, Agent, or Firm* — Blank Rome LLP (57) ABSTRACT

A method for improving mobility and/or the quality of synovial fluid of an affected articular joint, wherein the joint is associated with at least a first muscle group and at least a second muscle group each having an antagonistic relationship for effecting mobility of the joint through a range of motion when recruited by natural neural impulses. The method includes positioning at least two first electrodes proximate to the at least first muscle group, positioning at least two second electrodes proximate to the at least second muscle group, and applying motor-level electrical stimulation to the at least first and second muscle groups via the at least two first and second electrodes in a multiphasic pattern corresponding to a sequence of electromyographic outputs.

20 Claims, 5 Drawing Sheets

(56) References Cited

U.S. PATENT DOCUMENTS

| | | | |
|---|---|---|---|
| 4,738,250 A | 4/1988 | Fulkerson et al. |
| 4,785,813 A | 11/1988 | Petrofsky |
| 4,976,264 A | 12/1990 | Petrofsky |
| 5,070,873 A | 12/1991 | Graupe et al. |
| 5,133,341 A | 7/1992 | Singer et al. |
| 5,269,304 A | 12/1993 | Matthews |
| 5,273,033 A | 12/1993 | Hoffman |
| 5,324,317 A | 6/1994 | Reiss |
| 5,350,415 A | 9/1994 | Cywinski |
| 5,387,231 A | 2/1995 | Sporer |
| 5,397,338 A | 3/1995 | Grey et al. |
| 5,458,565 A | 10/1995 | Tillinghast, III et al. |
| 5,540,735 A | 7/1996 | Wingrove |
| 5,549,656 A | 8/1996 | Reiss |
| 5,562,718 A | 10/1996 | Palermo |
| 5,755,745 A | 5/1998 | McGraw et al. |
| 5,817,138 A | 10/1998 | Suzuki |
| 5,836,995 A | 11/1998 | MGraw et al. |
| 5,851,223 A | 12/1998 | Liss et al. |
| 5,947,913 A | 9/1999 | Palumbo |
| 5,947,914 A | 9/1999 | Augustine |
| 5,976,063 A | 11/1999 | Joutras et al. |
| 5,980,435 A | 11/1999 | Joutras et al. |
| 6,064,912 A | 5/2000 | Kenney |
| 6,393,328 B1 | 5/2002 | McGraw et al. |
| 6,456,884 B1 | 9/2002 | Kenney |
| 6,456,885 B1 | 9/2002 | Shiba et al. |
| 6,564,103 B2 | 5/2003 | Fischer et al. |
| 6,623,454 B1 | 9/2003 | Eggers et al. |
| 6,647,296 B2 | 11/2003 | Fischell et al. |
| 6,725,094 B2 | 4/2004 | Saberski |
| 6,988,005 B2 | 1/2006 | McGraw et al. |
| 7,035,691 B2 | 4/2006 | Campos |
| 7,257,448 B2 | 8/2007 | Crowe et al. |
| 7,468,264 B2 | 12/2008 | Brighton et al. |
| 7,783,348 B2 | 8/2010 | Gill et al. |
| 2003/0135129 A1 | 7/2003 | Cusimano et al. |
| 2004/0015207 A1 | 1/2004 | Barriskill et al. |
| 2004/0054379 A1 | 3/2004 | Carroll et al. |
| 2005/0010264 A1 | 1/2005 | Brighton et al. |
| 2006/0135900 A1 | 6/2006 | Ingimundarson et al. |
| 2007/0197946 A1 | 8/2007 | Gilmour |
| 2008/0208287 A1 | 8/2008 | Palermo et al. |

FOREIGN PATENT DOCUMENTS

| | | |
|---|---|---|
| JP | 2002514108 T | 5/2002 |
| JP | 2002191707 A | 7/2002 |
| JP | 2002200104 A | 7/2002 |
| WO | WO-9843560 A1 | 10/1998 |
| WO | WO-0103768 A1 | 1/2001 |
| WO | WO-2004023975 A2 | 3/2004 |
| WO | WO-2005087148 A1 | 9/2005 |
| WO | WO-2007019569 A2 | 2/2007 |

OTHER PUBLICATIONS

Hua Gu, "Direct Electric Acupuncture for Patella Chondromalacia: A Preliminary Report of a Clinical Study," Acupuncture Today, Oct. 2001, vol. 2, Issue 10.

Katayama Y. "Deep Brain Stimulation Therapy for Involuntary Movements," Rinsho Shinkeigaku, vol. 41, No. 12, Dec. 1, 2001, pp. 1079-1080.

Benabid et al., "Deep Brain Stimulation of the Corpus Luysi (Subthalamic Nucleus) and Other Targets in Parkinkson's Desease. Extension to New Indications Such as Dystonia and Epilepsy," J. Neurol., Sep. 1, 2001, 248 Supp. 3: III 37-47, 2 pages.

Allert et al., "Effects of Bilateral Pallidal or Subthalamic Stimulation on Gait in Advanced Parkinson's Disease," Mov. Disord., Nov. 1, 2001, 16(6): 1076-85, 2 pages.

Utti et al., "Extended Follow-up of Unillateral Deep Brain Stimulation for Tremor," P03.113; A220-221, 1 page.

Obwegeser et al., "Quantitative and Qualitative Outcome Measures After Thalamic Deep Brain Stimulation to Treat Disabling Tremors," Neurosurgery, 48(2); Discussion 281-4, 2001, 2 pages.

Obwegeser et al., "Simultaneous Thalamic Deep Brain Stimulation and Implantable Cardioverter-Defbrilator," Mayo. Clin. Proc., 76(1): 78-9, 2001, 2 pages.

Obwegesser et al., "Thalamic Stimulation for the Treatment of Midline Tremors in Essential Tremor Patients," Neurology, 54(12): 2342-4, 2000, 2 pages.

Oh et al., "Deep Brain Stimulator Electrodes Used for Lesioning: Proof of Principle," Neurosurgery, Aug. 1, 2001, 49(2): 363-7, Discussion 367-9, 2 pages.

Racette et al., "Thalamic Stimulation for Primary Writing Tremor," J. Neurol., May 1, 2001, 248(5):380-2, 2 pages.

Rocchi et al., "Effects of Deep Brain Stimulation and Levodopa on Postural Sway in Parkinson's Disease," J. Neural. Neurosurg. Psychiatry, Sep. 2002, 73(3):267-74, 2 pages.

Nasser et al., "Deep Brain Stimulation of VIM Thalamic Nucleus for Tremor Control," Arq. Neuropsiquiatr., Jun. 2002, 60(2-B):429-34, 1 page.

Racette et al., "Ipsilateral Thalamic Stimulation After Thalamotomy for Essential Tremor. A Case Report.," Stereotact Funct. Neurosurg. Jan. 1, 2000, 75(4):155-9; 2 pages.

Maya Pines, "New Imaging Techniques That Show the Brain at Work: Brain Scans That Spy on the Senses," Seeing, Hearing, and Smelling the World, A Report from the Howard Hughes Medical Institute, 2 pages.

Maya Pines, "New Imaging Techniques that Show the Brain at Work: The Next Generation of Brain Scans," Seeing, Hearing, and Smelling the World, A Report from the Howard Hughes Medical Institute, 2 pages.

Oregon Imaging Article, "P.E.T. Scan—Patient Information," 2 pages, www.oregonimaging.com/patient/petinfo.com.

Cigna Corporation, "Positron Emission Tomography (PET) Scans—Medicare Coverage," All States, GR 99-4, Jul./Aug. 1999, 7 pages.

Rezai et al., "Neurostimulation Systems for Deep Brain Stimulation: in Vitro Evaluation of Magnetic Resonance Imaging-Related Heating at 1.5 Tesla," J. Magn. Reson. Imaging, Mar. 1, 2002, 15(3):241-50, 2 pages.

Mobile PET Systems, Inc. "Clinical Applications," 5 pages.

Neurological Associates, Inc. "Deep Brain Stimulation," 6 pages, www.wvneuro.com/deep%20brain%20stimulation.htm.

Hamza et al., "Effect of the Duration of Electrical Stimulation on the Analgesic Response in Patients with Low Back Pain," Anesthesiology, Dec. 1999, vol. 91, No. 6, pp. 1622-1627.

Ghoname et al., "The Effect of Stimulus Frequency on the Analgesic Response to Percutaneous Electrical Nerve Stimulation in Patients with Chronic Low Back Pain," Anesthesia & Analgesia, vol. 88, No. 4, Apr. 1999, pp. 841-846.

Seroussui et al., "Effectiveness of Percutaneous Neuromodulation Therapy for Patients with Chronic and Severe Low Back Pain," Pain Practice, vol. 3, Issue 1, 2003, pp. 22-30.

Ghoname et al., "Percutaneous Electrical Nerve Stimulation for Low Back Pain," JAMA, vol. 281, No. 9, Mar. 3, 1999, pp. 818-823.

Robinson et al., "Clinical Elecrophysiology, Electrotherapy and Electrophysiologic Testing," Second Edition, Williams & Wilkins, pp. cover, 285, 288-290.

Johnson et al., "An In-Depth Study of Long-Term Users of Transcutaneous Electrical Nerve Stimulation (TENS). Implications for Clinical Use of TENS.," Pain, vol. 41, 1991, pp. 221-229.

Han et al., "Effect of Low- and High-Frequency TENS on Met-Enkephalin-Arg-Phe and dynorphin A Immunoreactivity in Human Lumbar CSF," Pain, vol. 47, 1991, pp. 295-298.

Nelson et al., Editors, "Clinical Electrotherapy," third edition, Appelton & Lange, Stamford, Connecticut, pp. cover, 316-319.

Peer Review Network, Inc., "Special Report: Vertis Percutaneous Neuromodulation Therapy (PNT)," PRN Newsletter, vol. 9, No. 6, Nov. 2002, pp. 1-5.

Gopalkrishnan et al., "Effect of Varying Frequency, Intensity, and Pulse Duration of Transcutaneous Electrical Nerve Stimulation on Primary Hyperalgesia in Inflamed Rats," Arch. Phys. Med. Rehabil., vol. 820, Jul. 2000, pp. 984-990.

(56) References Cited

OTHER PUBLICATIONS

Johnson et al., "Analgesic Effects of Different Frequencies of Transcutaneous Electrical Nerve Stimulation on Cold-Induced Pain in Normal Subjects," Pain, vol. 39, 1989, pp. 231-236.

Marchand et al., "Modulation of Heat Pain Perception by High Frequency Transcutaneous Electrical Nerve Stimulation (TENS)," The Clinical Journal of Pain, vol. 7, 1991, pp. 122-129.

Baker L (1993). Applications of NMES with Traditional Treatment Programs. *NeuroMuscular Electrical Stimulation* A Practical Guide 3$^{rd}$ ed., pp. 169-185. Downey: Los Amigos research & Education Institute, Inc.

Dieppe P, et al. (2000). Osteoarthritis. *Clinical Evidence*, 3: 529-541.

Lane NE, Thompson JM (1997). Management of Osteoarthritis in the primary-care setting: An evidence-based approach to treatment. *American Journal of Medicine*, 103 (6A): 25S-30S.

Wise C (1999). Osteoarthritis. In DC Dale, DD Federman, eds., *Scientific American Medicine*, vol. 1, part 1, chap. 15,pp. 1-7. New York: Scientific American.

Cooper C, Coggon D (1999). Physical activity and knee Osteoarthritis. Lancet 353(9171): 2177-2178.

\* cited by examiner

METHODS FOR IMPROVING MOBILITY AND CONTROLLING CARTILAGE MATRIX DEGRADATION OF WEIGHT-BEARING ARTICULAR JOINTS

CROSS REFERENCE TO RELATED APPLICATIONS

The present application is a continuation of U.S. patent application Ser. No. 12/016,914, filed Jan. 18, 2008, which is a continuation-in-part of U.S. patent application Ser. No. 10/659,278, filed Sep. 11, 2003, which claims the benefit of U.S. Provisional Patent Application Ser. No. 60/409,589, filed Sep. 11, 2002, the contents of which are hereby incorporated by reference in their entirety.

FIELD OF THE INVENTION

The present invention generally relates to degenerative joint disease and osteoarthritis and, more particularly, is related to methods for improving mobility and controlling cartilage matrix degradation of weight-bearing articular joints.

BACKGROUND OF THE INVENTION

Historically, electrical muscle stimulation has been employed to re-educate and re-train impaired muscles. The restoration of movement, especially in stroke paralysis, has seen limited success with what is known as functional electrical stimulation. The goal of functional electrical muscle stimulation is to restore functional capacity of muscles following a debilitating trauma. Primary candidates for functional electrical muscle stimulation include persons with paraplegia, hemiplegia and quadriplegia, as well as individuals with spinal cord injury or patients suffering from an impairment of the central nervous system, e.g., multiple sclerosis, head injury, or cerebral palsy.

U.S. Pat. No. 3,083,712 to Keegan relates generally to electrical muscle therapy, and more specifically to a programmed sequence for muscle therapy. It is an object of Keegan to provide an apparatus for producing sequential programming between antagonistic muscles in a proper time relation required for normal function of the muscles. In the illustrative example of Keegan, stimulation through an electrode is applied to the peroneal nerve, which causes muscle causes dorsiflexion and a slight eversion, i.e., turning out of the foot. In this example, the electrical stimulation is provided to assure that the toes of a foot will be lifted while the foot is being swung forward to avoid the dragging of the toes, dragging the toes being at the paralyzed side of the body while walking being characteristic of hemiplegics. The stimulation of the example is provided when a switch is depressed as the heel strikes the ground, thereby bridging contacts to provide energy from a battery source. Accordingly, the "sequential programming" of Keegan relates to a method for stimulating the peroneal nerve, not stimulating multiple muscles in a sequence. The functional movements caused, if at all, by this type of stimulation rarely become voluntary movements for the patient.

The ultimate goal for patients with spinal cord injury is to ambulate. Accordingly, muscles may be stimulated in the swing phase by electrical stimulation to advance the limb through its range of motion. Muscles are also stimulated during the stance phase so the patient can remain in the upright position. Despite the momentary recovery periods between swing and stance phases of a limb, fatigue sets in rapidly and muscles can simply fail due to the electrical stimulation's activation of fatigue-prone fast motor units. Fatigue may also prevail because disruptions of the spinal cord promote the conversion of slow fatigue-resistant to fast-fatigable muscle fibers, particularly in the weight-bearing muscles that cross single joints. Further, postural instability during such stimulation may cause falls. This instability is related to the small number of muscles stimulated by such electrical stimulation as compared to the total number of muscles that would normally require stimulation to advance a limb through its range of motion.

Accordingly, attempts have been made to overcome muscle failure due to fatigability and due to conversion of slow-twitch to fast-twitch muscle while a limb advances through its range of motion. U.S. Pat. No. 4,165,750 to Aleev et al. relates to a bioelectrically controlled electric stimulator of human muscles comprising an oscillator and a group of stimulator channels. Aleev uses a live person and functional electrical stimulation to improve the correspondence between movements actually performed by a human and programmed movements, to mitigate pain in the course of stimulation, and to make it possible to check the fatigability of muscles in the course of electric stimulation by changing the stimulation conditions at the onset of fatiguability. Aleev attempts to achieve these objects in a system that senses the bioelectric activity of the muscles of a programmer, manipulates the corresponding electric signal, and applies it to the muscles of a person whose movements are under control, all while continuing to sense the bioelectric activity of the muscles of the programmer. These objects are meant not only to restore the strength of damaged muscles, but also to restore lost motor skills, i.e. to enable a person to perform compound motions of the extremities, torso and head similar to those of a healthy person's extremities, torso and head.

U.S. Pat. No. 5,350,415 to Cywinski relates to a device for trophic stimulation of muscles that does not depend on muscle contraction to achieve a therapeutic result. The device of Cywinski contains a pulse generation circuit that mimics the motor unit action potentials (MUAPs) that are naturally generated when muscles are innervated. MUAPs are known to have a mean rate of firing between 5 and 15 pulses per second, which is far below the stimulation rate necessary to achieve fused and forceful contraction of muscle. An object of Cywinski is to stimulate a trophic change of muscle contractile properties from fast-fatiguing into slow fatigue resistant types. Accordingly, Cwyinski achieves this therapeutic result without causing fused and forceful contraction of a muscle.

Electrical stimulation can be patterned after the body's natural movements and is hereinafter referred to as "patterned electrical muscle stimulation. Patterned electrical muscle stimulation applies a template of the firing pattern recorded in a healthy limb as it moves through its range of motion. Patterned electrical muscle stimulation may also be patterned after the body's natural MUAPs or any other observable sequencing of muscles. For example, the intact biceps and the triceps muscles' activity pattern may be detected in the form of electromyographic output and recorded during the flexion of the straight arm. Then, the timing and amplitude parameters of these electromyographic activities (the synergy patterns) are analyzed. Using a mathematical model, the activity patterns are reconstructed and applied via an electrical muscle stimulator to the impaired muscle pair. When impaired muscles contract, a sensory stimulus pattern ascends to the brain where, in a way thus far unidentified, a new motor template is generated. Once the new motor template is available, voluntary functional movement may become possible.

The methods discussed above relate primarily to the treatment of impaired muscles. More recently, researchers are studying the physiological processes for bioelectrical interactions among, and the activity regarding the growth and repair of, certain tissues and cells other than muscles. For example, osteoarthritis, also known as degenerative joint disease, is characterized by degeneration of articular cartilage, as well as proliferation and remodeling of subchondral bone. The usual symptoms of osteoarthritis are stiffness, limitation of motion, and pain. Osteoarthritis most commonly affects the knee joint more so than any other articular joint. Articular joints are encapsulated in a protective sac-like structure called a bursa, and there is a lining of the joint called the synovium that produces synovial fluid. This synovial fluid bathes and lubricates the articular surfaces of the joints and helps protect the cartilage. Synoviocytes and other cells found in the joint spaces adjacent to cartilage also have an important role in cartilage metabolism, e.g., synoviocytes produce metalloproteinases that are capable of breaking-down cartilage.

The breakdown of cartilage that is seen in conditions of osteoarthritis occurs in several stages. First, the synovial fluid becomes thinner and loses its elasticity and viscosity, which decreases its ability to cushion the joint. Without this cushioning effect, the cartilage in the joint may be more likely to "wear down." Therefore, the surface of the smooth cartilage covering the joint softens and begins to lose its ability to absorb the impact of movement and can be more easily damaged from excess use or shock. The joint may also lose its shape as the cartilage breaks down, and bony growth or bone spurs may form on the edges of the affected joint compartment. As a result, small particles of bone and cartilage may degrade and begin to float around in the joint space, which contributes to the further degradation of the affected joint. Thus, one factor for measuring the effectiveness of methods of treatment for osteoarthritis may be the quantitative and qualitative analyses for measuring the viscosity and density of synovial fluid.

While some clinical studies have shown electrical muscle stimulation to reduce joint pain, the actual effectiveness of electrical muscle stimulation in reducing or reversing joint deterioration has been questioned based on the efficacy criteria used in such studies.

Thus, there is a need to demonstrate through the measurement of better efficacy criteria and actual physical indicia that patterned muscle stimulation has a beneficial effect on degenerative joint disease and osteoarthritis.

SUMMARY OF THE INVENTION

In response to the deficiencies of prior methods of electrical stimulation, it is a non-limiting objective of the present invention to employ a method for improving mobility and/or the quality of synovial fluid of an affected articular joint, wherein the joint is associated with at least a first muscle group and at least a second muscle group each having an antagonistic relationship for effecting mobility of the joint through a range of motion when recruited by natural neural impulses. The method includes positioning at least two first electrodes proximate to the at least first muscle group, positioning at least two second electrodes proximate to the at least second muscle group, and applying motor-level electrical stimulation to the at least first and second muscle groups via the at least two first and second electrodes in a multiphasic pattern corresponding to a sequence of electromyographic outputs.

In accordance with the above method, the step of applying the motor-level electrical stimulation may include applying the motor-level electrical stimulation while the joint is in a position to minimize at least one of pressure and moving friction in the joint such that the weight-bearing load and moving friction of the joint is contemporaneously minimized during the step of applying the motor-level electrical stimulation.

According to another aspect of the above method, the step of applying motor-level electrical stimulation in a multiphasic pattern may include beginning a first phase of applying motor-level electrical stimulation to the at least first muscle group and ending the first phase of applying, beginning a second phase of applying motor-level electrical stimulation to the at least second muscle group before ending the first phase of applying and ending the second phase of applying after ending the first phase of applying, beginning a third phase of applying motor-level electrical stimulation to the at least first muscle group before ending the second phase applying and stopping the third phase of applying, and repeating the first phase of applying, the second phase of applying, and the third phase of applying.

It is another non-limiting objective of the present invention to employ a system for improving mobility and/or the quality of synovial fluid of an affected articular joint, wherein the joint is associated with at least a first muscle group and at least a second muscle group each having an antagonistic relationship for effecting mobility of the joint through a range of motion when recruited by natural neural impulses. The system includes an electro-medical device configured to apply motor-level electrical stimulation in a multiphasic pattern via at least a first channel and at least a second channel, the multiphasic pattern being programmed into the electro-medical device and corresponding to the sequence of an electromyographic output for the joint, at least two first electrodes connected to the at least first channel of said electro-medical device, the at least two first electrodes being positioned proximate to the at least first muscle group, and at least two second electrodes connected to the at least second channel of said electro-medical device, the at least two second electrodes being positioned proximate to the at least second muscle group.

In accordance with the above system, the electro-medical device may be further configured to apply at least one of interferential stimulation, transcutaneous electrical nerve stimulation, high volt galvanic stimulation or micro-current stimulation via the at least first channel and the at least second channel. The interferential stimulation may be sensory-level pre-modulated interferential electrical stimulation.

According to another aspect of the above system, the step of applying motor-level electrical stimulation in a multiphasic pattern includes may include the pattern described above.

BRIEF DESCRIPTION OF THE DRAWINGS

Many aspects of the present invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION OF THE PREFERRED EMBODIMENTS

Non-limiting embodiments of the present invention utilize patterned electrical muscle stimulation to improve mobility of and to control cartilage matrix degradation in affected, weight-bearing, articular joints.

Referring to the drawings, wherein like reference numerals represent like parts throughout the various drawing figures, reference numeral 100 is directed to an affected, weight-bearing, articular joint by applying motor-level patterned muscle electrical stimulation using an electro-medical device 110. A deformation of the joint 100 occurs upon the administration of the patterned muscle stimulation by sequential contraction of the muscles 112, 114 associated with the joint 100. The sequential contraction of the muscles 112, 114 produces forces that are transmitted into the joint 100, ultimately causing a naturally sequenced deformation of the joint 100. The deformation of the joint 100 subjects the joint 100 to conditions that naturally enhance vegetative function without incurring weight-bearing load.

Figure 1:
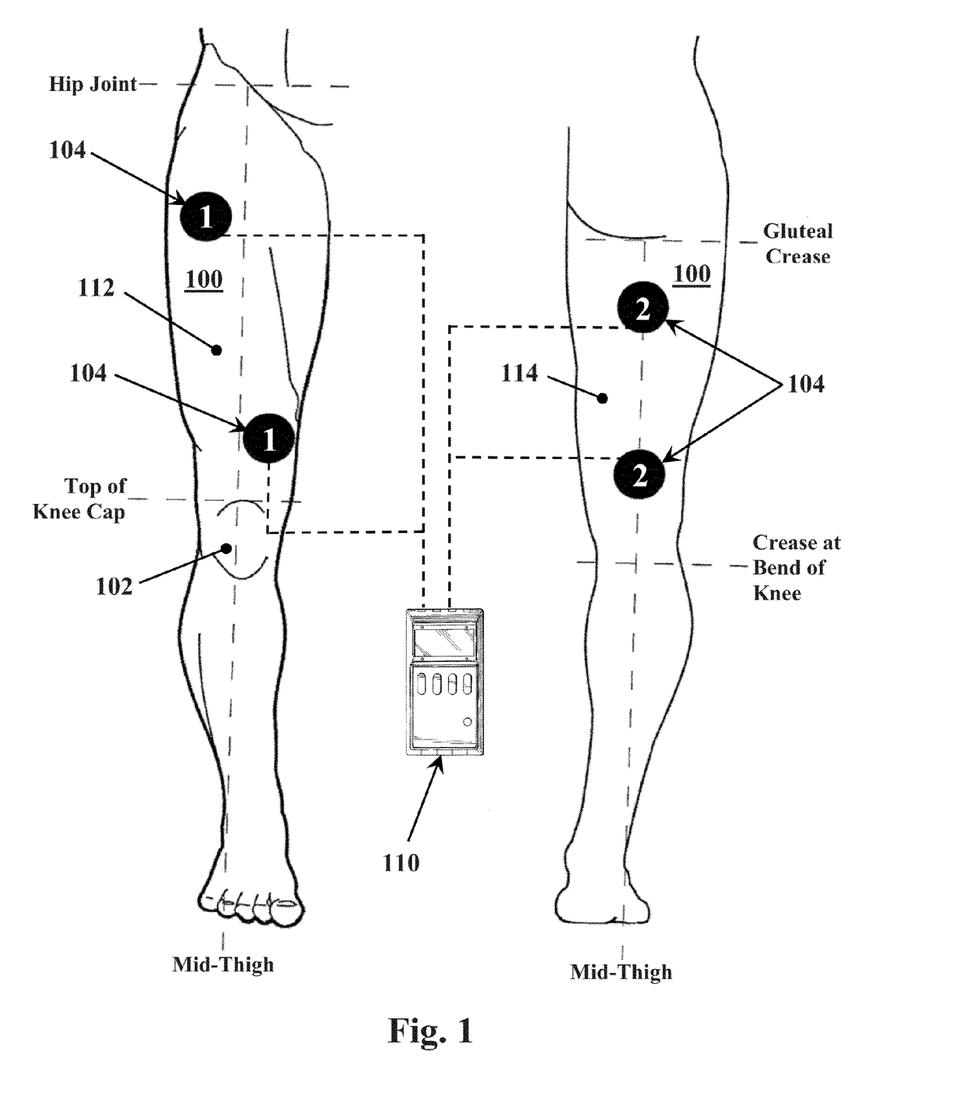
FIG. 1 is a front-side and back-side view of a weight-bearing articular joint illustrating the placement of surface skin electrodes to promote motor-level electrical stimulation in a triphasic pattern based on an electromyographic output for stimulating the antagonistic muscle groups associated with the joint.

FIG. 1 illustrates a method for improving mobility of and controlling cartilage matrix degradation of an affected articular joint 100, specifically a knee joint 102, by applying motor-level patterned muscle electrical stimulation using surface skin electrodes 104. The surface skin electrodes 104 may be placed at predetermined locations such that the electrical stimulation pattern corresponds to the sequence of electrical discharges in individual muscle cells which contract together to perform compound motions during natural movements of a non-affected knee joint.

With continuing reference to FIG. 1, the surface skin electrodes 104 may be placed on a muscle group on the front area of the thigh 112 and a muscle group on the back area of the thigh 114. More specifically, on the front area of the thigh 112, one electrode may be placed over the vastus lateralis and one electrode may be placed over the vastus medialis, these two muscles making up a first muscle group or the quadriceps on the front area of the thigh 112. On the back area of the thigh 114, one electrode may be placed over the proximal biceps femoris and one electrode may be placed over the distal biceps femoris, these two muscles making up a second muscle group, or the hamstrings generally, on the front area of the thigh 114.

The surface skin electrodes 104 may be connected to an electro-medical device 110 for supplying the electrical stimulation signals utilizing multiple channels. An exemplary electro-medical device 110, such as the electrical stimulator disclosed by McGraw et al. in U.S. Pat. No. 6,393,328 and U.S. Pat. No. 6,988,005, the disclosures of which are incorporated herein by reference, is described in more detail below.

Figure 3:
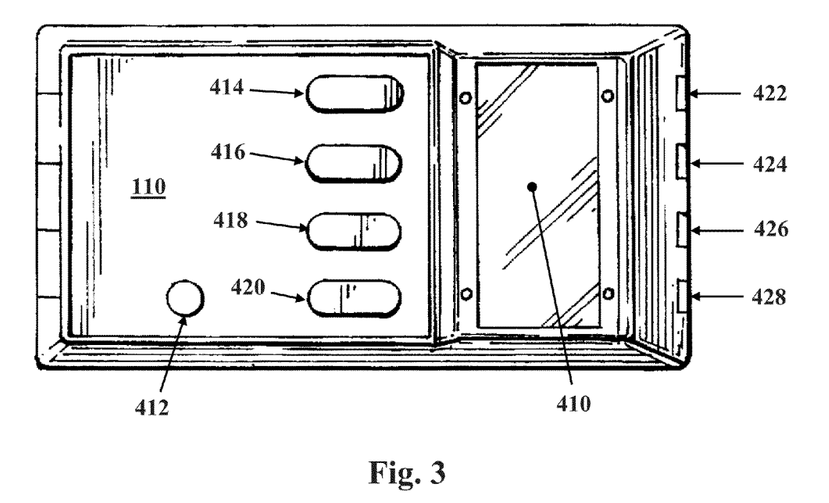
FIG. 3 is a top view of an exemplary embodiment of an electro-medical device of the present invention.

FIG. 3 illustrates an exemplary embodiment of such a portable muscle stimulator. As shown in FIG. 3, the electro-medical device 110 may include a liquid crystal display (LCD) 410 to provide visual feedback and an interface for the user to determine the type, level and length of electrical stimulation treatment. The electro-medical device 110 may also include a power switch 412 and four switches 414-420 for controlling the respective outputs of each of four isolated channels contained in the electro-medical device 110. Four output jacks 422-428 may be provided at the front of the electro-medical device 110, a separate jack for each of up to four electrically isolated output channels that are capable of independently treating four separate muscle groups. Each of the electrically isolated channels may have a separate intensity control for independently increasing and decreasing the intensity of stimulation provided by that channel. Additionally, the electro-medical device may be provided with a programmable data storage card that provides usage monitoring capability so that it can be easily and safely used by an unsupervised patient, such as the data card disclosed by McGraw et al. in U.S. Pat. No. 5,836,995 and U.S. Pat. No. 5,755,745, the disclosures of which are incorporated herein by reference.

With reference to FIGS. 1 and 3, the pair of surface skin electrodes 104 placed on the front area of the thigh 112 correspond to channel 1 and the pair of surface skin electrodes 104 placed on the back area of the thigh 114 correspond to channel 2. The electro-medical device is adapted to provide multiple types and levels of stimulation through each of its four channels.

In an embodiment of the invention, the application of the electrical stimulation occurs by employing a symmetrical waveform via pairs of surface skin electrodes 104 electrically connected to separate channels of an electro-medical device 110. The symmetry of the waveform allows the pairs surface skin electrodes 104 for each channel to operate with anode and cathode interchangeability. Alternatively, the electrical stimulation may employ asymmetrical waveforms such that the surface skin electrodes 104 for the pairs at each channel correspond individually to an anode or a cathode, without interchangeability.

Figure 2:
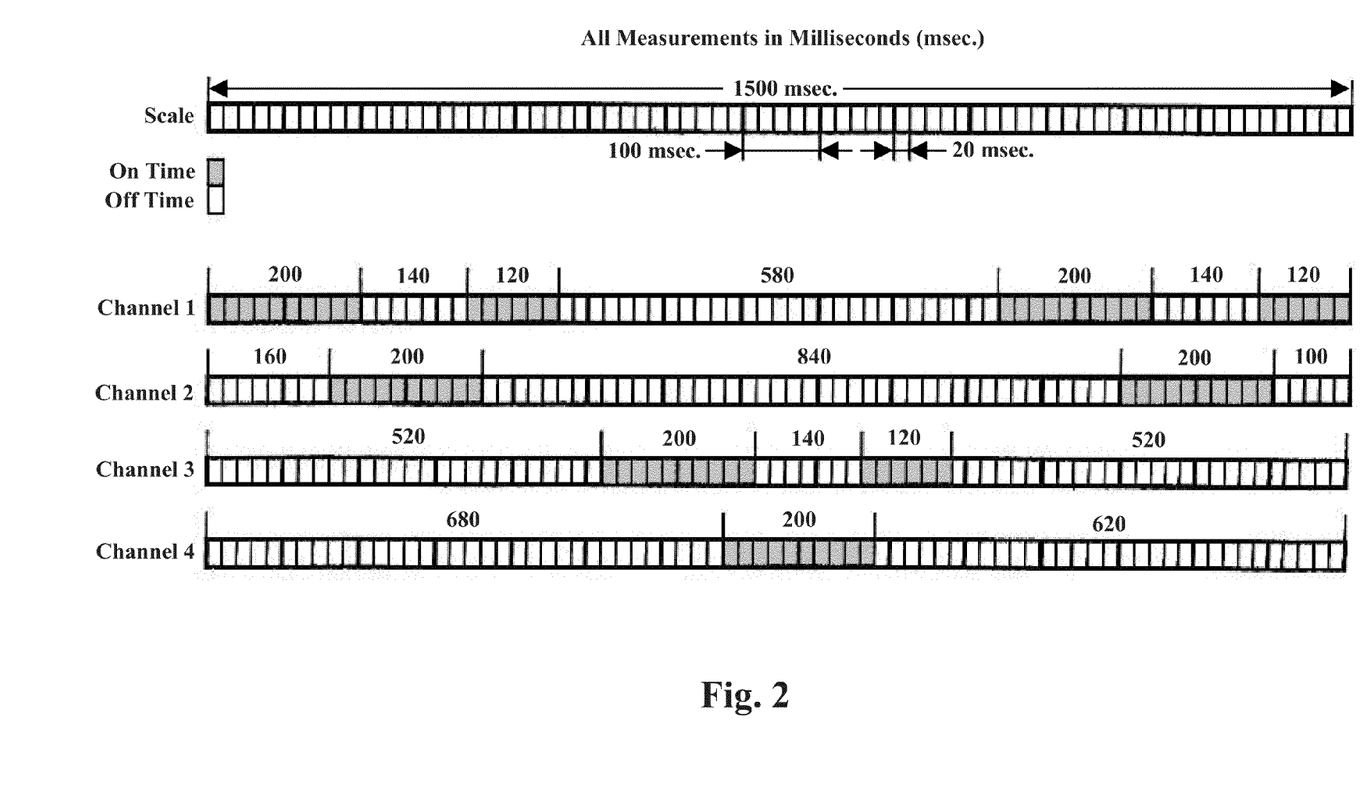
FIG. 2 illustrates the relative timing pattern of sequenced current, as applied to antagonistic muscle groups of an articular joint.

In the non-limiting configuration of FIGS. 1-3, the electrical stimulation may be applied to each muscle group of the affected articular joint 100 at the motor-level, causing the muscles to contract. In an exemplary embodiment of the present invention, the motor-level stimulation may have a parameter set that causes an action potential to be generated at a nerve or muscle of the affected joint 100. The parameter set may form a biphasic, symmetrical waveform that modulates frequency, amplitude, and/or phase to produce a period of action potentials sufficient to cause strong, visible contractions of the stimulated muscle, but without actually causing the articular joint 100 to move through its full range of motion, i.e., without causing functional electrical stimulation.

The motor-level electrical stimulation may be provided in a multi-phase, or multiphasic, pattern. In the non-limiting embodiments described hereinafter, the electrical stimulation is described with reference to a pattern including three phases, i.e., a triphasic pattern. As illustrated in FIG. 2, the motor-level patterned muscle stimulation is provided in a triphasic pattern that includes stimulating the quadriceps, then the hamstrings and back again to the quadriceps. The first phase of the three phase stimulation sequence causes the contraction of the quadriceps. As the quadriceps nearly complete their contractions, the hamstrings begin to be stimulated, causing contraction of the hamstrings. There is a period of overlap between phase 1 and 2 of the three phase stimulation where both the quadriceps and hamstrings are stimulated at the same time. As the hamstrings nearly complete their contractions, the quadriceps are again stimulated. Similar to phase 1 and 2, there is a period of overlap between phase 2 and 3 of the three phase stimulation. This sequence produces the normal vegetative functions of the knee 102, such as production of synovial fluid without further degradation of the knee 102. The knee 102 incurs no additional weight-bearing load or increase in moving friction during the stimulation.

FIG. 2 is a chart that illustrates the relative timing pattern of sequenced current, as applied to antagonistic muscle groups of an articular joint 100. The chart of FIG. 2. illustrates the "on time" and "off time" for applying motor-level stimulation to each muscle group. The "on time" corresponds to a period of applying electrical stimulation and is represented by the shaded in areas of the graph, and the "off time" corresponds to a period of not applying electrical stimulation.

In an embodiment of the sequential firing pattern illustrated in FIG. 2, the on and off times for channels 1 and 2 respectively correspond to the periods of electrical discharge across the quadriceps and hamstring muscles. The firing pattern of FIG. 2 emulates the timing pattern of muscular contractions as electromyographically recorded from the quadriceps and hamstrings of a weight-bearing, articular joint completing a full range of motion (not shown). According to the present invention, electromyographic outputs (not shown) were recorded from live motor nerves while in a state of high-level activity, e.g., motor nerves of the quadriceps and hamstrings measured while the live subject was running. The timing pattern for which the muscle groups contract can then be reproduced, as shown in FIG. 2, for synthetic electrical stimulation. The electrical stimulation is delivered by the electro-medical device 110 in a pattern that is based on the timing of the pattern of the live motor nerves. As the patterned muscle stimulation is applied, the affected joint 100 is subjected to conditions that allow it to undergo vegetative functionality without actually causing the joint to move through its biologically designed range of motion.

In another embodiment of the sequential firing pattern illustrated in FIG. 2, the on and off times for channels 1 and 2 respectively correspond to the periods of electrical discharge across the quadriceps and hamstring muscles of a first leg while the on and off times for channels 3 and 4 correspond to the periods of electrical discharges across the quadriceps and hamstring muscles of a second leg. Electrical stimulation, therefore, may be applied to an affected knee joint 102 of each leg at the same time using an electro-medical device 110 having at least four stimulation channels 1-4. In this non-limiting embodiment, the surface skin electrodes 104 corresponding to channel 1 may be placed on the front area 112 of a first leg; the surface skin electrodes 104 corresponding to channel 2 may be placed on the back area 114 of the first leg; the surface skin electrodes 104 corresponding to channel 3 may be placed on the front area 112 of a second leg; and the surface skin electrodes 104 corresponding to channel 4 may be placed on the back area 114 of the second leg.

Applying motor-level stimulation to muscle groups associated with a specific joint in an sequence that mimics an electromyographic output pattern can control cartilage matrix degradation by causing contractions in the muscle groups associated with the affected joint without causing the affected joint to move through its full range of motion. This promotes blood flow in the joint and associated muscle groups without causing grinding and friction which are contributing factors to cartilage matrix degradation. Also in the non-limiting configuration of FIG. 2, the electrical stimulation may be applied to an affected joint 100 while the joint 100 is in a position that minimizes pressure and moving friction therein, such as applying the stimulation to the knee joint 102 while the person is sitting or lying down. This further allows stimulation that mimics normal activities of daily living, such as walking or running, without producing the type of destructive wear and tear on the joints that would normally occur in a weight-bearing position while walking or running.

With continuing reference to the configuration of FIG. 1, interferential current may also be delivered using the four surface skin electrodes 104. In applying a known type of interferential current called pre-modulated interferential current, the two currents are mixed in the electro-medical device 110 before being delivered to the patient's skin via the electrodes 104. In a conventional application for delivering true interferential currents, the interferential currents can be produced endogenously in the patient. The pre-modulated delivery, in contrast to conventional true interferential current, offers an ease of application. The clinical difference between the two delivery methods is not significant if discernible at all.

In one embodiment, pre-modulated interferential stimulation is applied first, using the electrode 104 placement in the present invention. Then, motor-level patterned muscle stimulation is applied second. Both pre-modulated interferential stimulation followed by the patterned muscle stimulation can be delivered via the electro-medical device 110 in a single treatment session. Since the electrode 104 placement is the same for both types of stimulation for the present invention, the patient will not need to adjust or change electrode 104 placements. Pre-modulated interferential stimulation delivered followed by patterned muscle stimulation may improve the effectiveness of the patterned muscle stimulation because of the interferential stimulation's ability to decrease sensitivity to the higher intensities of patterned muscle stimulation.

It should be understood by one of ordinary skill that other alternative types of electrical stimulation can be used before and after the patterned muscle stimulation treatment to enhance effectiveness. Examples of these types of stimulation include, but are not limited to, Transcutaneous Electrical Nerve Stimulation (TENS), Interferential Stimulation, Diadynamic Stimulation, High Volt Galvanic Stimulation (HVGS), Electro-Magnetic and Pulsed Electro-Magnetic Field Stimulation (EMF & PEMF) and Micro-current Stimulation.

In any of the exemplary embodiments, the duration of each type of stimulation may be from about 10 minutes to about 4 hours per day. Further, when interferential stimulation is applied at a sensory level, it may be applied in a range from 0.1 mA to 150 mA as rated into a 500 Ohm load. Interferential stimulation may also be applied with a resulting beat frequency between 0 and 250 Hz with a base frequency between 1 and 20 KHz. When motor-level stimulation is applied in a pattern based on a sequence of electromyographic output, it may be applied in a range from 5 mA to 150 mA as rated into a 500 Ohm load. Stimulation may be applied at a constant intensity from the beginning of the "on time" to the end of the "on time," with no stimulation being provided during the "off time." To allow smoother transitions between "off times" and "on times," stimulation may be ramped up to a specific intensity at the beginning the "on time" and ramped back down to zero at the end of the "on time" as disclosed in U.S. Pat. No. 6,393,328 and U.S. Pat. No. 6,988,005.

Additionally, in applying the method of the present invention, proper and reproducible placement of the surface skin electrodes 104 may be facilitated through the use of an applicator. The applicator is intended to allow the surface skin electrodes 104 to be positioned on the muscles associated with the affected joint 100 in a manner reproducible each time it is worn by providing predetermined locations therein for positioning the surface skin electrodes 104. The predetermined locations correspond to muscles associated with the affected joint 100 around which the applicator is to be worn. It is also contemplated that the surface skin electrodes 104 may be configured with alternative garments, such as stabilizers, compression units, slings, and the like that may minimize the movement of weight-bearing articular joints 100.

The present invention may be better understood with reference to the accompanying examples that are intended for purposes of illustration only and should not be construed to limit the scope of the invention, as defined by the claims appended hereto.

Example 1

Comparing the Benefits of Patterned Muscle Stimulation to TENS in the Treatment of Osteoarthritis of the Knee Degenerative joint disease and osteoarthritis are progressive disease processes that affect articular joints, including but not limited to, the hips, knees, ankles, toes, back, neck, and shoulders. Typically, the weight-bearing joints, such as the hips, knees and ankles are most affected by osteoarthritis. The most common type of arthritis is osteoarthritis of the knee. More than 10 million Americans suffer from osteoarthritis of the knee, with most of those affected being older than 45 years of age. Pathologic changes in degenerative joint disease and osteoarthritis involve the progressive breakdown of the articular cartilage matrix.

A total of 116 patients who qualified for inclusion in this investigation were enrolled in one of five medical centers in the United States. The patients were randomly placed into "test" and "sham-control" stimulation groups and blinded to their assignment. The clinicians too were blinded to the stimulation group assignment in order to allow them to act as independent observers and evaluators. The study was completed after the 8-week assessment with a total of 101 patients.

During this investigation, the test group received a daily 35 minute session of stimulation, which consisted of 15 minutes of pre-modulated interferential stimulation, followed by 20 minutes of motor-level patterned muscle stimulation. During the pre-modulated interferential stimulation, the patients were asked to increase the intensity of the stimulation until experiencing a gentle tingling feeling on the skin, but not muscular contraction. The pre-modulated interferential stimulation had a base frequency of 5000 Hz and a pre-modulated beat frequency sweeping between 1 and 150 Hz. After 15 minutes of pre-modulated interferential stimulation, motor-level patterned muscle electrical stimulation was applied to the test group. The stimulation was as triphasic stimulation pattern that included stimulating to the point of contraction, the quadriceps, hamstrings and quadriceps, in that specific order with periods of intermittent overlap. This pattern was based on an electromyographic output of the normal contraction patterns and timing of the quadriceps and hamstrings during a high-level running activity. Patients were instructed to increase the intensity of the motor-level stimulation until feeling a mild but comfortable muscular contraction, and after five minutes to turn up the intensity to produce a moderate to strong contraction that could be tolerated without causing pain. The motor-level patterned muscle stimulation delivered 50 Hz impulses for 200 milliseconds every 1500 milliseconds, while stimulation amplitude was fixed at 60 mA and patients controlled stimulation intensity by varying the pulse width, with intensity settings varying from 0.08 C to 11.38 C.

During each low-current TENS session for patients in the sham-control group, stimulation was delivered as a square wave with a 0.2 Hz frequency and a fixed amplitude of 60 mA, with pulse width adjusted to provide a net output of 73 nC. During the TENS stimulation, the patients were told that the stimulation might be perceived but would not produce a muscular contraction (i.e., that stimulation would be at a sensory level but not at a motor level). Patients receiving low-current TENS stimulation were also told that the intensity of the stimulation was preset and that adjustments had no effect on the actual current.

The primary efficacy criteria included the pain, physical function and stiffness subscales of the Western Ontario MacMaster (WOMAC) Osteoarthritis Index and Visual Analog Scales (VAS) for pain and quality of life. The WOMAC used in this study was the Likert version 3.1 standardized with English for an American population, consisting of 24 self-administrated questions that were answered for each item on a 5-point Likert scale (none, mild, moderate, severe and extreme). The 24 questions were reported under three separate subscales: pain, physical function, and stiffness. The pain subscale had five questions scored 0 to 4 and was considered invalid if more than one item was missing; hence, it had a range of 0 (no pain) to 20 (maximal pain). In the event of a missing item, the remaining four items were averaged and then multiplied by 5. The function subscale had 17 questions scored 0 to 4 and was considered invalid if more than three items were missing; hence, it had a range of 0 (maximal function) to 68 (minimal function). In the event of missing items, the remaining items were averaged and then multiplied by 17. The stiffness subscale had two items scored 0 to 4 and was considered invalid if either was missing; hence, it had a range from 0 (no stiffness) to 8 (maximal stiffness). In the event of a missing item, the score for remaining item was multiplied by 2.

VAS lines were used for measuring overall pain intensity and global impact of osteoarthritis on quality of life. The VAS line for overall pain rating was anchored at one end with a "0" and the label "No Pain" and at the other end with a "100" and the label "Worst Pain Imaginable." The VAS line for the quality of life rating was anchored at one end with a "0" and the label "Very Poor" and at the other end with a "100" and the label "Very Good." Patients were instructed to place a mark on the respective VAS lines to report the intensity or quality of the sensation being experienced. VAS ratings were provided for both knees.

Figure 4:
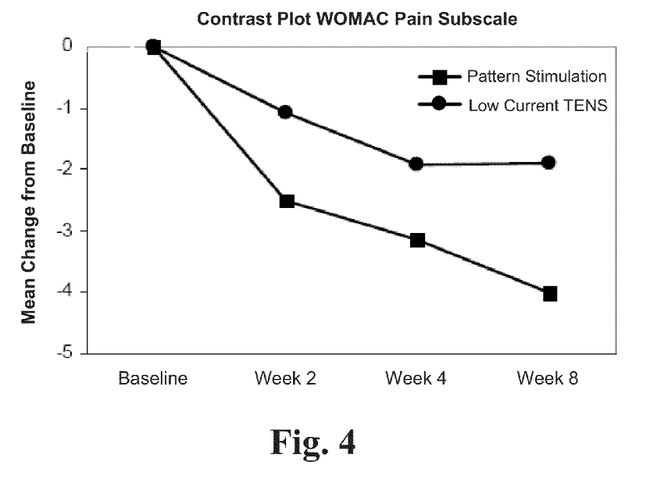
FIG. 4 is a contrast plot illustrating the WOMAC subscale of pain score in Example 1.
Figure 5:
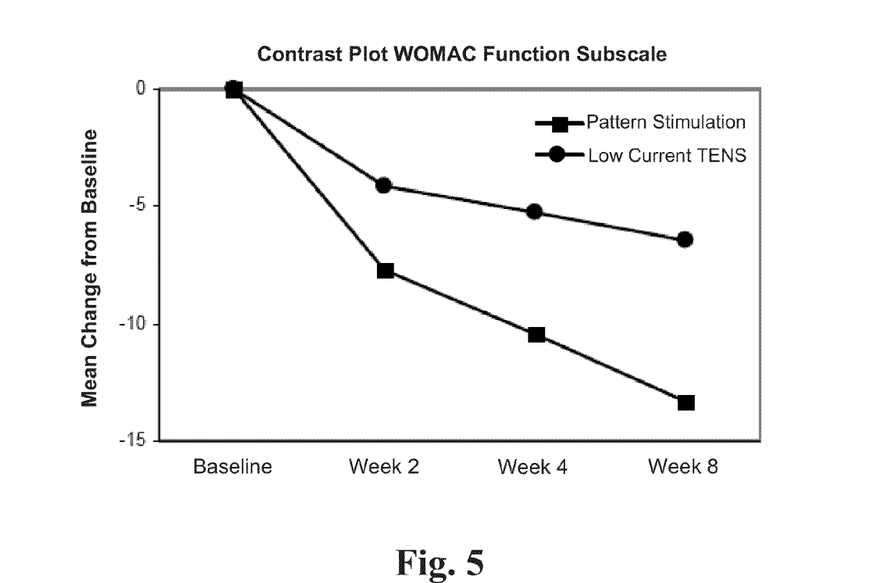
FIG. 5 is a contrast plot illustrating the WOMAC subscale of function score in Example 1.
Figure 6:
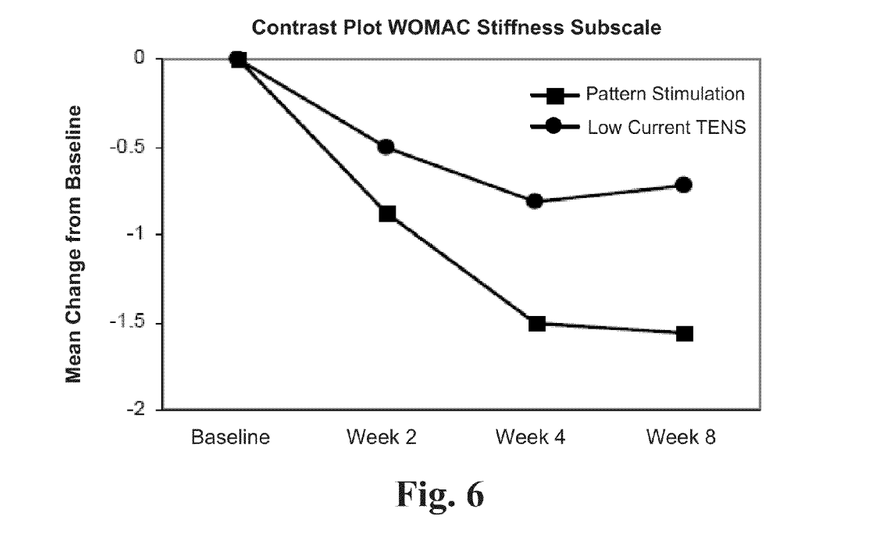
FIG. 6 is a contrast plot illustrating the WOMAC subscale of stiffness score in Example 1.

The scores based on the WOMAC and VAS efficacy criteria were expressed as a baseline mean value measured prior to the first stimulation session and a value of mean change from that baseline value measured in the subsequent eight weeks. A lower mean change from baseline was indicative of less impact on osteoarthritis. In the eight-week treatment data, statistically significant differences for each of the three WOMAC subscales favored the method of the present invention. Specifically, the test and sham-control groups had comparable baseline means for each of the three WOMAC subscales (P values >0.5). Patients in the test group had significantly greater reduction than patients in the sham-control group in the WOMAC pain subscale (3.98 vs. 1.90; P=0.002), physical function subscale (12.86 vs. 6.74; P=0.003), and stiffness subscale (1.53 vs. 0.74; P=0.004) after 8 weeks of treatment. FIG. 4 illustrates the contrast between test and sham-control groups in the WOMAC pain subscale at each scheduled visit; FIG. 5 illustrates the contrast between test and sham-control groups in the WOMAC physical function subscale at each scheduled visit; and FIG. 6 illustrates the contrast between test and sham-control groups in the WOMAC stiffness subscale at each scheduled visit. This data demonstrates that pre-modulated interferential stimulation followed by motor-level patterned muscle stimulation of the present invention is significantly more efficient than conventional low-current TENS in relieving pain, increasing function, and decreasing stiffness.

The WOMAC reduction values for each of the three subscales, when viewed as a percentage of each other within each subscale, further exemplify the superiority of pre-modulated interferential stimulation followed by motor-level patterned muscle stimulation over conventional low-current TENS. In the pain subscale for the test group, the reduction value (3.98) divided by the number of questions for the pain subscale (5) equals 80%. For the sham-control group the reduction value (1.90) divided by the number of questions for the pain subscale (5) equals 38%. As a percentage of each other, the test group percentage (80%) minus the sham-control group percentage (38%) divided by the sham-control group percentage (38%) equals 110%. This indicates that pain in the test group was 110% reduced to that in the sham-control group.

In the physical function (difficulty performing daily activities) subscale of WOMAC reduction values, the test group reduction value (12.86) divided by the number of questions for the difficulty performing daily activities subscale (17) equals 76%. For the sham-control group the reduction value (6.74) divided by the number of questions for the difficulty performing daily activities subscale (17) equals 40%. As a percentage of each other, the test group percentage (76%) minus the sham-control group percentage (40%) divided by the sham-control group percentage (40%) equals 90%. This indicates that difficulty performing daily activities in the test group was 90% reduced to that in the sham-control group.

In the stiffness subscale of WOMAC reduction values, the test group reduction value (1.53) divided by the number of questions for the stiffness subscale (2) equals 77%. For the sham-control group the reduction value (0.74) divided by the number of questions for the stiffness subscale (2) equals 37%. As a percentage of each other, the test group percentage (77%) minus the sham-control group percentage (37%) divided by the sham-control group percentage (37%) equals 108%. This indicates that stiffness in the test group was 108% reduced to that in the sham-control group.

Although the test and sham-control groups also had comparable baseline means for both VAS ratings, the mean changes from baseline to last visit in quality of life VAS rating were similar between the test and sham-control groups (18.17 vs. 18.16; P=0.99) while patients in the test group had a greater decrease in the overall pain VAS (27.91 vs. 23.19; P=0.29) after eight weeks of treatment. The difference between the overall pain VAS in the treatment groups, however, did not achieve statistical significance. On the other hand, if only patients who completed the study (49 in the test group and 50 in the sham-control group) were included in the analysis, the difference between groups in mean change from baseline increased from 4.71 to 9.40 for overall pain VAS rating and achieved statistical significance (P=0.038). While the collective data did not achieve a statistical difference in the overall pain VAS assessment, it was not expected that overall pain and quality of life VAS would achieve statistical significance. Unlike WOMAC, which is a test specifically designed for osteoarthritis of the knee, VAS assessment are tests for general purposes and less accurate in measuring osteoarthritis of the knee than WOMAC.

Additionally, two secondary effectiveness analyses, which included only patients who completed the study, were performed for the WOMAC pain and function scale. The first analysis assessed the interaction of treatment group by time. The mean change from baseline to each scheduled visit for the two treatment groups were contrasted. The results showed that at the Week 2 visit, patients in the test group already had significantly greater reduction in WOMAC subscales of pain (2.50 vs. 1.08; P=0.008) and function (7.74 vs. 4.14; P=0.03) than patients in the sham-control group. This result demonstrates that pre-modulated interferential stimulation followed by patterned muscle stimulation of the present invention has a beneficial effect after only two weeks of stimulation while conventional single-stage low-current TENS did not.

The other secondary effectiveness analysis compared the frequency of sham-control group and test group patients who reported 20% or more improvement in WOMAC scores in two post-baseline visits. The results of the comparison showed that a higher percentage of patients in the test group had improvement for WOMAC subscales of pain (71.2% vs. 49.1%; P=0.023) and function (65.4% vs. 45.3%; P=0.030) than patients in the sham-control group. Therefore, the results of the two secondary effectiveness analyses mirrored the primary analyses, favoring of the method of the present invention over single-stage low-current TENS.

The analysis of this carefully controlled clinical investigation provides scientific evidence that the method of the present invention is safe and effective for use in treating patients with osteoarthritis of the knee. Specifically, the results provide statistically significant evidence that the method of the present invention reduces pain in a knee joint affected with osteoarthritis. This statistically significant evidence was in the form of improvements on the WOMAC subscales of pain, physical function and stiffness.

Example 2

The Effect of Sequential Electrical Stimulation on Osteoarthritis

An animal model was used for quantitative analyses of the components of synovial fluid that affect cartilage matrix degradation.

In an investigation on adult hound dogs, subjects were selected from dogs housed at Washington State University and under the care of personnel from the Comparative Orthopedic Research Laboratory (CORL). Each dog had a cartilage defect made previously and had established osteoarthritis in one of two stifle joints. Based on this criteria, a total of 11 adult hound dogs (six female and five male) were enrolled in the study.

The selected subjects, each being identified with a unique six-letter alphabetical identification tag, were randomly placed into "test" and "control" stimulation groups of five each, with one dog serving as the spare to replace a dog that might develop complications from surgery. Veterinary technicians placed the electrodes on both groups and applied stimulation to the test groups, with the technicians that took experimental measurements being blinded to the stimulation group assignment so as to allow them to act as independent observers and evaluators. The study interval was 12 weeks in length with the subjects in both groups receiving a single session of 30 minutes of treatment on a daily basis for six days per week during the 12-week period. The test group received 30 minutes of motor-level patterned muscle stimulation while the control group had the electrodes placed on them for 30 minutes without applying any electrical stimulation.

A single technician observed and recorded the subjects' pain on a VAS scale and measured the subjects' ground reaction forces using a force plate at baseline and on a weekly basis thereafter. Synovial fluid was collected from the affected joint of each subject at baseline and on a bi-weekly basis thereafter. Whenever synovial fluid was collected, 20 units of chymopapain were injected into the affected joint to maintain moderate lameness throughout degradation of the affected joint. Synovial fluid was collected only bi-weekly so that the weekly VAS scores and ground reaction force measurements could be evaluated for possible attenuation of lameness in the face of the chymopapain injections. This method of evaluation also made it possible to compare the synovial fluid data to the ground reaction force data at time points that matched that of the non-chymopapain weeks. In addition to this data, radiographs were taken of the affected joint at the beginning and end of the 12-week treatment. As a final source of data, a biopsy of osteochondral plug, i.e., bone or cartilage, was taken from each of the lateral and medial condyles in the affected body segment of each subject, both before and after the stimulation session.

The primary efficacy criteria for the ground reaction force data included Peak Vertical Force (PVF) and Vertical Impulse (VI). Ground reaction force data were recorded using a force plate capable of measuring stance time, propulsion impulse, breaking impulse, peak propulsion force, peak breaking force, peak vertical and vertical impulse forces. A pain score on a scale of 0 to 10 was used to measure overall pain. The pain score scale and criteria are adapted from a pain scoring system for evaluation of pain in dogs. (Can Vet J Volume 44, 2003 643-648).

Collected synovial fluid was assayed for sulfated glycosaminoglycans, hyaluronic acid, matrix metalloproteinase-3, albumin and soluble collagen. Due to a paucity of the synovial fluid collected from some of the subjects during the study, samples were group pooled to allow a large enough volume to run the analyses for the different synovial markers.

Biopsies of the osteochondral plugs were performed under general anesthesia and subjected to a histopathology evaluation. The evaluation focused on the condition of the articular cartilage and subchondral bone, and the severity of inflammation and fibrosis with a 0 to 4 semi-quantitative scoring system, with the higher score corresponding to a more prominent feature. The difficulty to consistently obtain osteochondral plugs from the medial and lateral condyle of the affected body segments, however, impacted the histopathological evaluation of the changes at tissue level. The histology sections prepared along the long axis of the biopsies sometimes showed no presence of articular cartilage (four of 18 in the control group and three of 22 in the test group). Therefore, the analyses focused on the trend of anatomical indices of improvement rather than statistics.

Improvements in anatomical indices were determined from the appearance of chondrocytes in the hypertrophic zone of the hyaline type articular cartilage using a Safranin O stain assay for determining the normal amounts of glycosaminoglycans. Articular cartilage has columns of chondrocytes arranged in an orderly fashion as layers of proliferative and hypertrophic chondrons without clustering, i.e., multiple chondrocytes in one chondron. Subchondral bone was distinguished from articular cartilage by observing that subchondral bone would have properly spaced trabeculae with appropriate thickness and marrow contents without inflammation and fibrosis. The stronger and closer the staining of the cartilage was to the color red, the greater the indication that the cartilage contained a normal amount of glycosaminoglycans.

The ground force reaction data were analyzed and expressed as a baseline mean value measured prior to the first stimulation session of Week 0 and a value of mean change from that baseline value measured in the subsequent 12 weeks. A greater percentage change from baseline was indicative of a positive response to the method of the present invention. In the 12-week treatment data, however, there was no significant percentage change from baseline in PVF or VI scores within each group over time, but there was a graphic trend for the test group to perform better than the control group after each week of stimulation sessions. Specifically, there was a major graphic trend for the test group to have a greater PVF and VI scores over the control group after each stimulation session, on both chymopapain injection weeks and non-chymopapain injection weeks. This data demonstrates that the motor-level patterned muscle stimulation of the present invention improves behavior indices such as PVF and VI in adult hound dogs with osteoarthritis as compared to adult hound dogs with osteoarthritis that receive no stimulation to their affected articular joints.

The weekly VAS scores were correlated with the corresponding weekly measurements of percent mean change of PVF and VI to evaluate a possible attenuation of lameness in the face of chymopapain on chymopapain injection weeks. There was a significant negative correlation between VAS scores and both PVF measurements (Pearson Correlation Coefficient=−0.70725, $p<0.0001$) and VI measurements (Pearson Correlation Coefficient=−0.70402, $p<0.0001$). This negative correlation demonstrates that where overall pain decreased in the test group, PVF and VI values increased. The low p-value demonstrates that the measurements taken on chymopapain injection weeks were consistent with those taken on non-chymopapain injection weeks.

The synovial fluid was analyzed for the presence of markers such as sulfated glycosaminoglycans, hyaluronic acid, matrix metalloproteinase-3, albumin and soluble collagen, with a decrease in the presence these markers being indicative of a positive response to the method of the present invention. In the 12-week treatment data, however, there was no significant change in the presence of the synovial fluid markers within each group over time, but there was a graphic trend for the test group to have less sulfated glycosaminoglycans, hyaluronic acid, and matrix metalloproteinase-3 in their synovial fluid than the control group after every two week period of stimulation sessions. In addition to there being a strong graphic trend for a positive effect in decreasing sulfated glycosaminoglycans, graphic trends confirmed a positive significance between the test group and control group at T12 ($p=0.0026$) for albumin concentrations and at T6 ($p=0.0001$), T10 ($p<0.0001$), and T12 ($p<0.0001$) for soluble collagen concentrations. The decrease in soluble collagen within the synovium was 20% compared to the control group. This data demonstrates that the motor-level patterned muscle stimulation of the present invention improves the quality of synovial fluid in adult hound dogs with osteoarthritis as compared to adult hound dogs with osteoarthritis that receive no stimulation to their affected body segments by reducing the amount of glycosaminoglycans, albumin and soluble collagen in synovial fluid.

For paired comparison between the pre-treatment and the post-treatment biopsies, three pairs from the control group and four pairs from the test group were used to measure anatomical indices of osteoarthritis. The severity of inflammation and fibrosis in the marrow and synovium between the pre-treatment and the post-treatment biopsies increased in the control group, while both parameters remained similar in the treated group (not statistically different). The subchondral bone showed mixed features of increased erosion by osteoclasts in some samples and compensatory sclerotic thickening of trabeculae in others. The pattern of change in the morphology of articular cartilage on the lateral condyle improved in the test group, from a negative average (degenerative) to a positive average (repairing), and deteriorated in the control group. The improvements were determined from the relatively normal appearance of chondrocytes in the hypertrophic zone of the hyaline type articular cartilage and the strong red staining of Safranin O for glycosaminoglycans. The subchondral bone of the lateral condyle in the test group seemed to have thickness and space near normal condition. The medial condyle of the test group, however, had similar morphological features in pre- and post-treatment conditions.

As illustrated in FIGS. 7A-8B, photomicrographs demonstrate the differences in pre- and post-treatment of the test and control and control groups. These histology slides were prepared from the biopsies through a process of decalcification in formic acid, dehydration and embedding in paraffin, staining with Safranin O and counter-staining with fast green. The cartilage appeared orange to red while bone appeared in light bluish green. Cellularity in the marrow represented the inflammatory infiltration, accompanied by fibrosis.

Figure 7A:
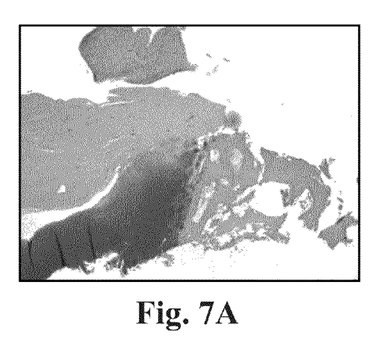
FIG. 7A is a photomicrograph illustrating a histology of a baseline biopsy of lateral condyle control group obtained in Example 2.
Figure 7B:
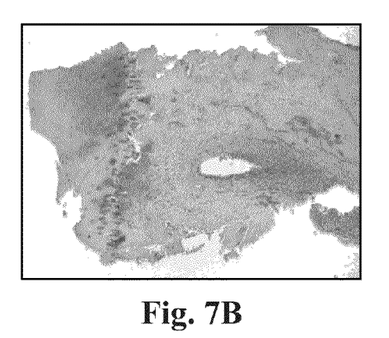
FIG. 7B is a photomicrograph illustrating a histology of a Week 12 biopsy of lateral condyle control group obtained in Example 2.
Figure 8A:
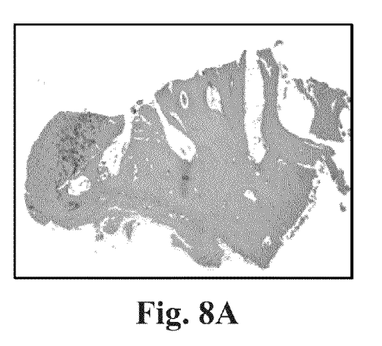
FIG. 8A is a photomicrograph illustrating a histology of a baseline biopsy of lateral condyle test group obtained in Example 2.
Figure 8B:
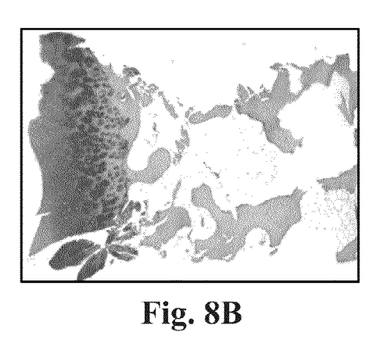
FIG. 8B is a photomicrograph illustrating a histology of a Week 12 biopsy of lateral condyle test group obtained in Example 2.

FIG. 7A illustrates a photomicrograph from a control group biopsy at baseline and FIG. 7B illustrates the corresponding photomicrograph from a biopsy from the same control group subject after Week 12. FIG. 8A illustrates a photomicrograph from a test group biopsy at baseline and FIG. 8B illustrates the corresponding photomicrograph from a biopsy from the same test group subject after Week 12. FIG. 7B illustrates a decrease in cartilage from FIG. 7A as indicated by a decrease in the amount of orange and red shown in FIG. 7B. Comparatively, FIG. 8B illustrates an increase in cartilage from FIG. 8A as indicated by an increase in the amount of arrange and red shown in FIG. 8B. FIGS. 7A-8B therefore provide evidence that the pattern of change in the morphology of articular cartilage on the lateral condyle improved in the test group from a negative average to a positive average while it deteriorated in the control group.

The analysis of this carefully controlled investigation provides valid scientific evidence that the method of the present invention improves the quality of synovium fluid. Specifically, the results provide evidence that applying motor-level patterned muscle stimulation based on an electromyographic output of normal musculature activation-timing and sequential patterning decreases albumin and soluble collagen concentrations within the synovium fluid of the animal models' affected joints. The improvement indicates that matrix degradation from articular cartilage is attenuated in this osteoarthritis model. As compared to the control group, graphic trends of the synovial markers, ground reaction force data and the histopathological improvements support a positive effect on the clinical osteoarthritis condition of the subjects that underwent treatment per the method of the present invention. The results demonstrate the effectiveness of the present invention in treating established osteoarthritis by reducing the amount of glycosaminoglycans, albumin and soluble collagen in synovial fluid.

As demonstrated by the two Examples, methods and apparatus according to the non-limiting aspects of the present invention increase the mobility of weight-bearing articular joints that are affected by osteoarthritis, as well as control the progressive process cartilage matrix degradation. Statistically significant improvement in efficacy criterion measuring change in terms of WOMAC subscales of pain, function and stiffness support this conclusion. Graphic trends demonstrating decreases in glycosaminoglycans, and statistically significant less amounts of albumin and soluble collagen in synovial fluid also support this conclusion, providing physical indicia that establish the present invention's ability to improve the quality of synovial fluid. The clinical studies therefore provide scientific evidence that the present invention is an effective method for decreasing the progressive process of joint deterioration.

The instant invention may be embodied in other forms or carried out in other ways without departing from the spirit or essential characteristics thereof. The present disclosure and enumerated examples are therefore to be considered as in all respects illustrative and not restrictive, the scope of the invention being indicated by the appended claims, an all equivalency are intended to be embraced therein. One of ordinary skill in the art would be able to recognize equivalent embodiments of the instant invention and be able to practice such embodiments using the teaching of the instant disclosure and only routine experimentation.

What is claimed is:

1. A method for improving mobility of an affected articular joint, wherein the joint is associated with at least a first muscle group and at least a second muscle group each having an antagonistic relationship for effecting mobility of the joint through a range of motion when recruited by natural neural impulses, the method comprising:
   positioning at least two first electrodes proximate to the at least first muscle group;
   positioning at least two second electrodes proximate to the at least second muscle group; and
   applying motor-level electrical stimulation to the at least first and second muscle groups via the at least two first and second electrodes in a multiphasic pattern corresponding to a sequence of electromyographic outputs.

2. The method of claim 1, wherein the step of applying the motor-level electrical stimulation includes applying the motor-level electrical stimulation while the joint is in a position to minimize at least one of pressure and moving friction in the joint such that the weight-bearing load and moving friction of the joint is contemporaneously minimized during the step of applying the motor-level electrical stimulation.

3. The method of claim 1, wherein the sequence of electromyographic outputs corresponds to a pattern of electromyographic outputs recorded from antagonistic muscle groups recruited by natural neural impulses.

4. The method of claim 1, wherein the step of applying motor-level electrical stimulation is preceded by a step of applying at least one of interferential stimulation, transcutaneous electrical nerve stimulation, high volt galvanic stimulation or micro-current stimulation.

5. The method of claim 4, wherein the interferential stimulation is sensory-level pre-modulated interferential electrical stimulation.

6. The method of claim 1, wherein the step of applying motor-level electrical stimulation is followed by a step of applying at least one of interferential stimulation, transcutaneous electrical nerve stimulation, high volt galvanic stimulation or micro-current stimulation.

7. The method of claim 1, wherein the step of positioning the at least two first electrodes includes positioning such electrodes at a front area of a thigh and the step of positioning the at least two second electrodes includes positioning such electrodes at a back area of the thigh.

8. The method of claim 1, wherein the affected articular joint is a weight-bearing joint affected by osteoarthritis.

9. The method of claim 1, wherein the multiphasic pattern includes a period of time during which electrical stimulation is applied via the at least two first and the at least two second electrodes in an overlapping manner.

10. The method of claim 1, wherein
the step of positioning at least two first electrodes includes placing the at least two first electrodes in an applicator to be worn on the affected articular joint in at least two first predetermined locations that will be proximate to the at least first muscle group when the applicator is worn on the affected articular joint; and
the step of positioning at least two second electrodes includes placing the at least two second electrodes in the applicator in at least two second predetermined locations that will be proximate to the at least second muscle group when the applicator is worn on the affected articular joint.

11. A method for improving the quality of synovial fluid of an affected joint, the method comprising:
positioning at least two first electrodes proximate to the at least first muscle group;
positioning at least two second electrodes proximate to the at least second muscle group;
applying motor-level electrical stimulation to the at least first and second muscle groups via the at least two first and second electrodes in a multiphasic pattern corresponding to a sequence of electromyographic outputs.

12. The method of claim 11, wherein the step of applying motor-level electrical stimulation in a multiphasic pattern includes applying the stimulation in an amount effective for controlling at least one cartilage matrix degradation marker selected from a group consisting of sulfated glycosaminoglycans, albumin, and soluble collagen.

13. The method of claim 11, wherein the step of applying motor-level electrical stimulation includes applying the motor-level electrical stimulation while the joint is in a position to minimize at least one of pressure and moving friction in the joint such that the weight-bearing load and moving friction of the joint is contemporaneously minimized during the step of applying the motor-level electrical stimulation.

14. The method of claim 11, wherein the sequence of electromyographic outputs corresponds to a pattern of electromyographic outputs recorded from antagonistic muscle groups recruited by natural neural impulses.

15. The method of claim 11, wherein the multiphasic pattern includes a period of time during which electrical stimulation is applied via the at least two first and the at least two second electrodes in an overlapping manner.

16. The method of claim 11, wherein
the step of positioning at least two first electrodes includes placing the at least two first electrodes in an applicator to be worn on the affected articular joint in at least two first predetermined locations that will be proximate to the at least first muscle group when the applicator is worn on the affected articular joint; and
the step of positioning at least two second electrodes includes placing the at least two second electrodes in the applicator in at least two second predetermined locations that will be proximate to the at least second muscle group when the applicator is worn on the affected articular joint.

17. A system for improving mobility of an affected articular joint, wherein the joint is associated with at least a first muscle group and at least a second muscle group each having an antagonistic relationship for effecting mobility of the joint through a range of motion when recruited by natural neural impulses, the system comprising:
an electro-medical device configured to apply motor-level electrical stimulation in a multiphasic pattern via at least a first channel and at least a second channel, the multiphasic pattern being programmed into the electro-medical device and corresponding to the sequence of an electromyographic output for the joint;
at least two first electrodes connected to the at least first channel of said electro-medical device, the at least two first electrodes being positioned proximate to the at least first muscle group; and
at least two second electrodes connected to the at least second channel of said electro-medical device, the at least two second electrodes being positioned proximate to the at least second muscle group.

18. The system of claim 17, wherein the joint is in a position to minimize at least one of pressure and moving friction in the joint such that the weight-bearing load and moving friction of the joint is contemporaneously minimized during the step of applying the motor-level electrical stimulation.

19. The system of claim 17, wherein the multiphasic pattern includes a period of time during which electrical stimulation is applied via the at least two first and the at least two second electrodes in an overlapping manner.

20. The system of claim 17, further comprising an applicator to be worn on the affected articular segment, wherein the at least two first electrodes are disposed in the applicator in at least two first predetermined locations that will be proximate to the at least first muscle group when the applicator is worn on the affected articular joint and the at least two second electrodes are disposed in the applicator in at least two second predetermined locations that will be proximate to the at least second muscle group when the applicator is worn on the affected articular joint.

* * * * *